United States Patent [19]
Ohta

[11] Patent Number: 5,096,290
[45] Date of Patent: Mar. 17, 1992

[54] APPARATUS FOR IMAGING FINGERPRINT USING TRANSPARENT OPTICAL MEANS HAVING ELASTIC MATERIAL LAYER

[75] Inventor: Naoya Ohta, Tokyo, Japan

[73] Assignee: NEC Corporation, Tokyo, Japan

[21] Appl. No.: 576,200

[22] Filed: Aug. 27, 1990

Related U.S. Application Data

[63] Continuation of Ser. No. 234,668, Aug. 22, 1988, abandoned.

[30] Foreign Application Priority Data

Aug. 21, 1987 [JP] Japan .................. 62-208727
Dec. 29, 1987 [JP] Japan .................. 62-336042

[51] Int. Cl.$^5$ ............................... G06K 9/00
[52] U.S. Cl. ................................ 356/71
[58] Field of Search ................ 356/71; 382/4

[56] References Cited

U.S. PATENT DOCUMENTS

| | | | |
|---|---|---|---|
| 3,174,414 | 3/1965 | Myer | 356/71 X |
| 4,120,585 | 10/1978 | DePalma et al. | 356/71 |
| 4,428,670 | 1/1984 | Ruell et al. | 356/71 |
| 4,537,484 | 8/1985 | Fowler et al. | 356/71 X |
| 4,544,267 | 10/1985 | Schiller | 356/71 |

*Primary Examiner*—Vincent P. McGraw
*Attorney, Agent, or Firm*—Sughrue, Mion, Zinn, Macpeak & Seas

[57] ABSTRACT

In order to obtain a clear surface pattern of an object such as a fingerprint impression and the like, a surface of an optical element against which the object is impressed is made of an elastic and/or viscous material. Thus, a surface pattern with high contrast is available even if the surface to be imaged is dry.

4 Claims, 8 Drawing Sheets

FIG. 3B (SWEAT OR WATER)

APPARATUS FOR IMAGING FINGERPRINT USING TRANSPARENT OPTICAL MEANS HAVING ELASTIC MATERIAL LAYER

This is a continuation of application Ser. No. 07/234,668 filed Aug. 22, 1988, now abandoned.

BACKGROUND OF THE INVENTION

1. Field of the Invention

This invention relates generally to an apparatus for use in imaging surface pattern impression and more specifically to such an apparatus which is highly suited for fingerprint imaging.

2. Description of the Prior Art

Various techniques for identifying individuals have been proposed and, among other things, fingerprint identification has proven one of the most reliable methods. An apparatus for identifying individuals through the use of fingerprint images, has been proposed wherein a fingerprint image is developed in the apparatus and automatically compared, using pattern recognition technique, with previously stored fingerprint images. Such an apparatus is provided with a fingerprint image acquisition terminal wherein a finger is placed in contact with a surface of an optical element internally illuminated (hereinafter, the surface of the optical element will sometimes be referred to as a window). The fingerprint image is obtained by utilizing the change in boundary conditions which occur on the surface or window on which a finger or thumb is placed. These known apparatus have been disclosed in Japanese patent applications which are provisionally published under publication Nos. 55-13446 and 58-144280, respectively.

Figure 1:
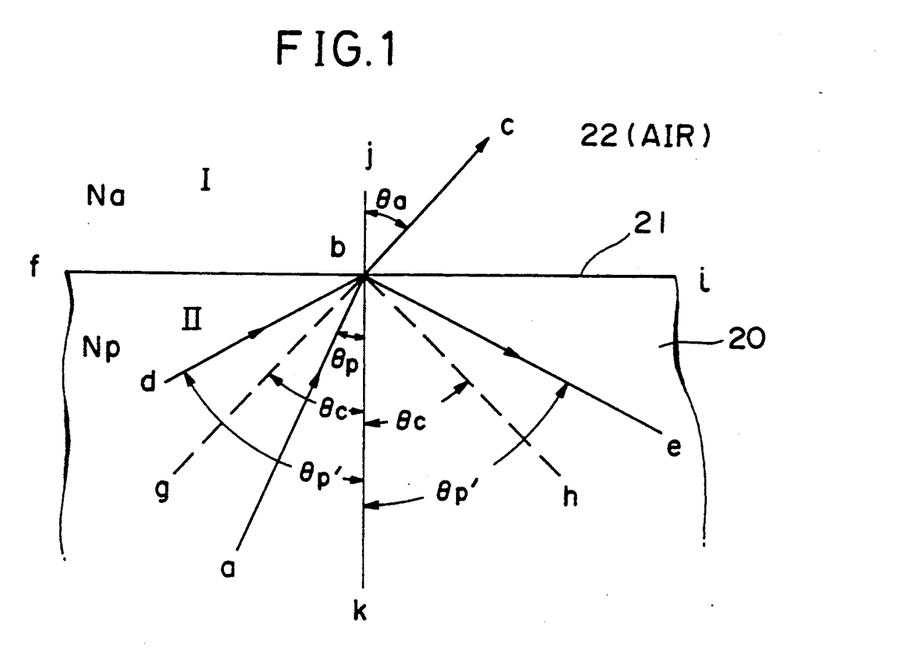
FIG. 1 is a schematic illustration of light rays refracted and reflected at a boundary surface between two different mediums.
Figure 2:
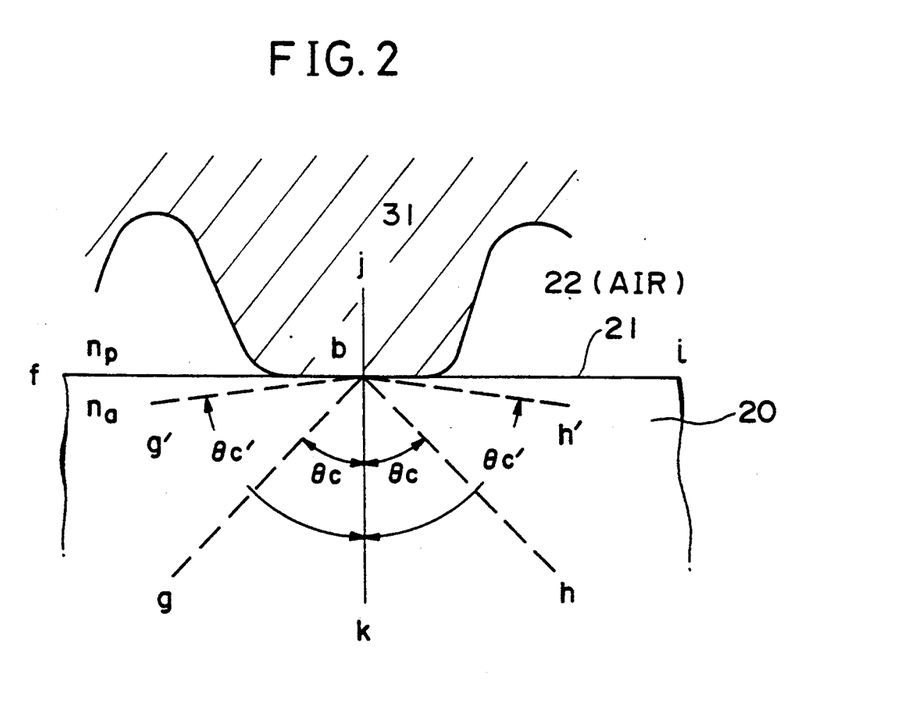
FIG. 2 is a diagram showing a critical angle ($\Theta c'$) at a boundary portion on which a finger is placed in comparison with a critical angle ($\Theta c$) in the case where a finger is not placed.

Before discussing in detail the known apparatus reference is firstly made to FIGS. 1 and 2. FIG. 1 shows light rays refracted and reflected at a boundary surface between two transparent substances I and II. In this instance I denotes air (refractive index Na) while II denotes an optical element which has a refractive index Np. In FIG. 1, a finger to be imaged is placed in contact with the surface or window 21 of the optical element 20. Assuming that Θp and Θa are respectively angles of incidence and refraction of a ray travelling along a path a-b-c, then the following equation is obtained using Snell's law.

$$Np \sin \Theta p = Na \sin \Theta a$$

It should be noted that in FIG. 1 each of Θp and Θa is less than a critical angle Θc. Further, if a ray "d" is incident on the boundary surface at a point "b" at an angle Θp' greater than Θc, then it is totally internally reflected and travels in the optical element as shown by "e".

FIG. 2 illustrates a finger ridge 31 in contact with the surface 21 of the optical element 20. The refractive index of the surface of a finger is larger than that of air and is nearly equal to that of the optical element 20, so that a critical angle at the finger contact portion does not exist or approximates 90 degrees (denoted Θc' in FIG. 2). It is therefore understood that a ray incident on a finger ridge from the optical element 20 does not totally internally reflect if the angle of incidence is smaller than Θc'. In this case, part of the light ray incident on the finger ridge is absorbed in the finger, while the rest is reflected and scattered in various directions in the optical element 20.

With the above descriptions in mind, the two previously mentioned known apparatus will be discussed.

The first prior art arrangement is of non-scattering type and has been disclosed in the aforesaid Japanese patent application provisionally published under No. 55-13446. In this prior art, incident light rays are arranged to strike the surface of the optical element such that the light is totally internally reflected only at the portions where the finger ridges are not in direct contact with the window. A light receiving means (or a light detector) is placed in a manner to receive the totally internally reflected light, and hence a resultant fingerprint image wherein the ridges are dark and the background bright, is obtained.

On the other hand, the second prior art is of scattering type and has been disclosed in the above-mentioned Japanese patent application provisionally published under No. 58-144280. In this prior art, the incident rays strike the boundary surface such that any total reflection is not invited, and a light receiving means is positioned to receive only the rays scattered at the portions where finger ridges are in direct contact with the window. Therefore, the resulting fingerprint image is such that the finger ridge portions are bright on a dark background.

In the second prior art, however, if the incident rays are totally internally reflected only at the portions where finger ridges are not in contact, and, if the light receiving means is positioned to receive only the rays scattered at the finger ridges, the same fingerprint image can be obtained. That is to say, if the light source is positioned in a region defined by an angle <gbg' in FIG. 2 by way of example, and if the light detector is positioned within the same angle region, the light detector receives only the scattered light rays.

Figure 3A:
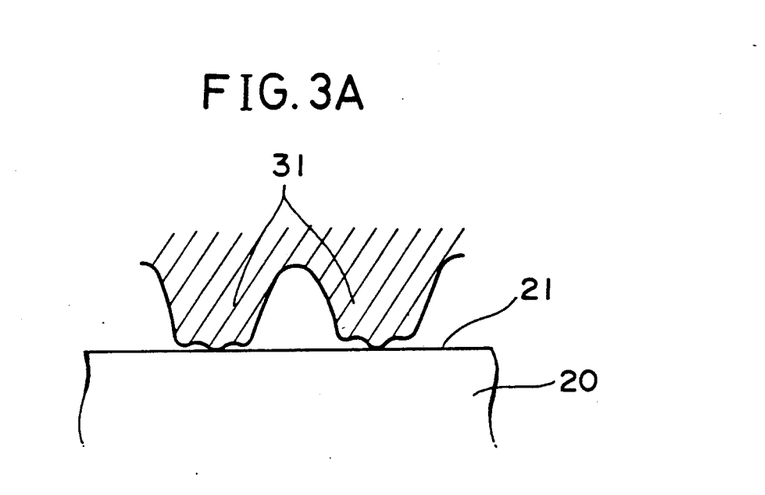
FIGS. 3A and 3B are illustrations in which a dry or wet finger is placed on a surface of an optical element.
Figure 3B:
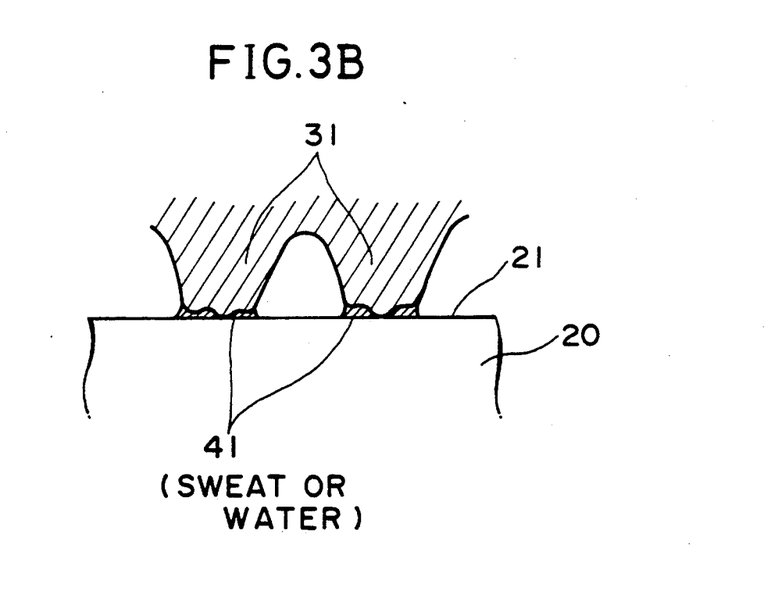

However, both of these conventional fingerprint imaging apparatus have encountered the problem that if a finger to be examined is dry it is impossible to obtain a clear fingerprint impression. This will be discussed in detail with reference to FIGS. 3(A) and 3(B). As shown in these microscopical views, the surface of a finger ridge is not flat and mirror-like but uneven as illustrated. As a consequence, if a finger is wet with sweat (for example), the spaces between the surfaces of a finger and the refractive surface 21 are filled with an aqueous liquid. Since the index of sweat or water is equal to or almost equal to that of the optical element 20, a clear fingerprint image can be obtained. However, on the contrary, in the case that a finger is dry, a fingerprint impression with high contrast is no longer expected because there exist a number of air layers between the surfaces of a finger ridge and the window 20.

SUMMARY OF THE INVENTION

It is an object of this invention to provide an improved apparatus for acquiring surface pattern impression in which a window on which a finger is placed is covered by a layer of a material which features a given amount of elasticity and/or viscosity.

More specifically, the present invention takes the form of an apparatus for imaging surface pattern of an object, comprising: a transparent optical means having a surface against which the object to be examined is impressed, the surface being made of an elastic and/or viscous material; a light source which directs light towards the surface of the transparent optical means;

and a light detector which receives light reflected from the surface of the transparent optical means.

BRIEF DESCRIPTION OF THE DRAWINGS

The features and advantages of the present invention will become more clearly appreciated from the following description taken in conjunction with the accompanying drawings in which like elements are denoted by like reference numerals and in which.

DETAILED DESCRIPTION OF THE PREFERRED EMBODIMENTS

This invention will hereinafter be described with reference to a fingerprint impression, but it should be noted that the instant invention is also highly suited for imaging other surface patterns such as seal impressions and the like.

A first preferred embodiment of this invention will be described with reference to FIGS. 4A, 4B, 5 and 6.

Figure 4A:
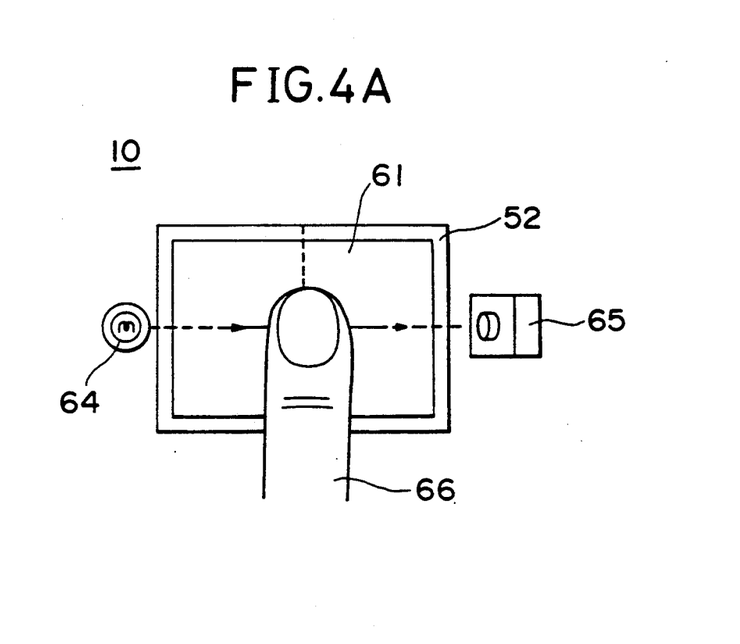
FIG. 4A is a plan view of an fingerprint imaging apparatus according to the first embodiment of this invention.
Figure 4B:
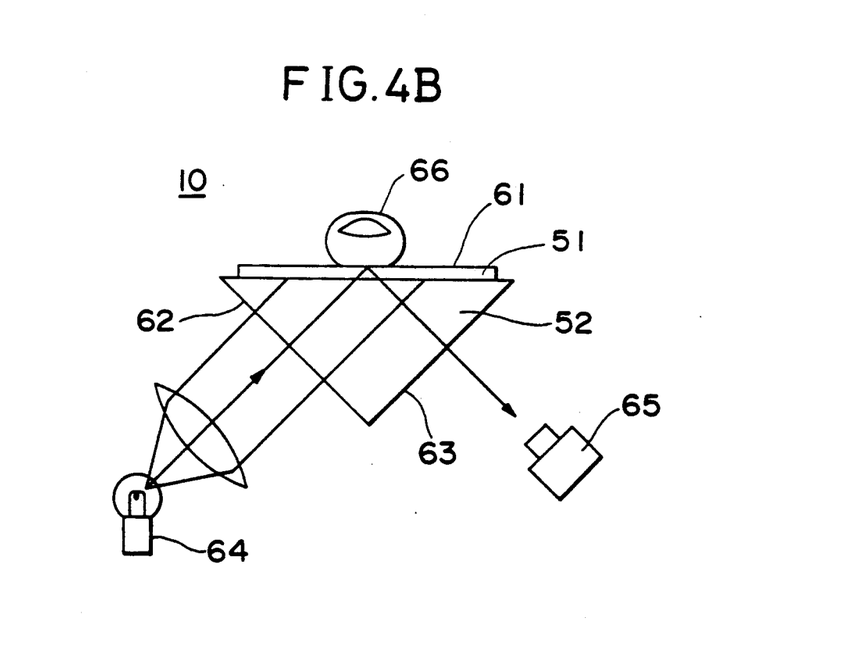
FIG. 4B is an elevation view of the apparatus shown in FIG. 4A.

FIG. 4A is a schematic plan view of a fingerprint imaging apparatus 10 according to this invention, with a finger 66 to be examined being placed in contact with a surface or window 61 of a layer 51 (see FIG. 4B). This layer is made of an elastic and/or viscous material, or, in other words, is made of a pliant material. FIG. 4B is a schematic elevation of the fingerprint imaging apparatus 10 shown in FIG. 4A. The feature of the instant invention resides in the provision of the layer 51. By way of example only, the layer may be formed of either natural and synthetic rubbers, the latter including silicon, epoxy and the like type elastomers.

The apparatus 10 further includes an optical element 52 made of suitable transparent material such as glass or plastics, a light source 64, and a light receiving means (or a light detector) 65. The element 52 is arranged in the form of a so-called porro prism in this embodiment. The first embodiment is of the non-scattering or reflecting type. That is to say, the light detector 65 receives essentially only the light rays which are totally internally reflected at the boundary 61. Light rays emitted from the light source 64 pass through a first face 62 of the prism 52 and strike the boundary 61 as shown in FIG. 4B.

Figure 5:
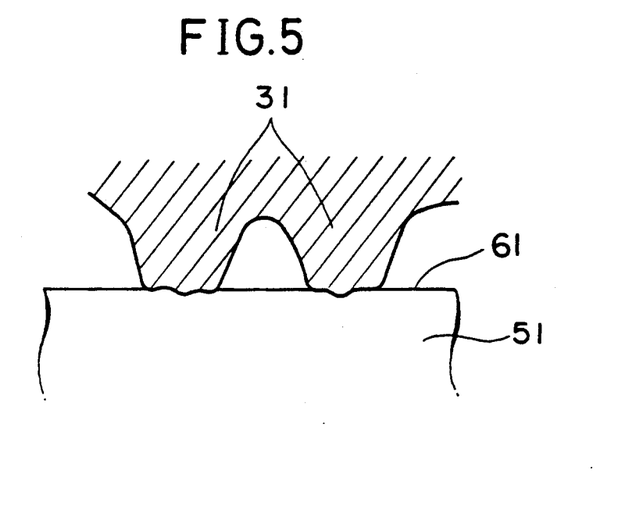
FIG. 5 is a diagram showing finger ridges pressed onto a layer according to this invention.

As shown in FIG. 5, when a finger is pressed against the layer 51, small recesses or hollows or the like, which exists on a finger ridge and form spaces between the finger ridge and the surface 61, are filled with the elastic and/or viscous material of the layer 51, thereby providing optical boundary conditions similar to those obtained with a wet finger. The refractive index of the layer 51 is preferably equal to that of optical element 52, but is not necessarily limited thereto.

Figure 6:
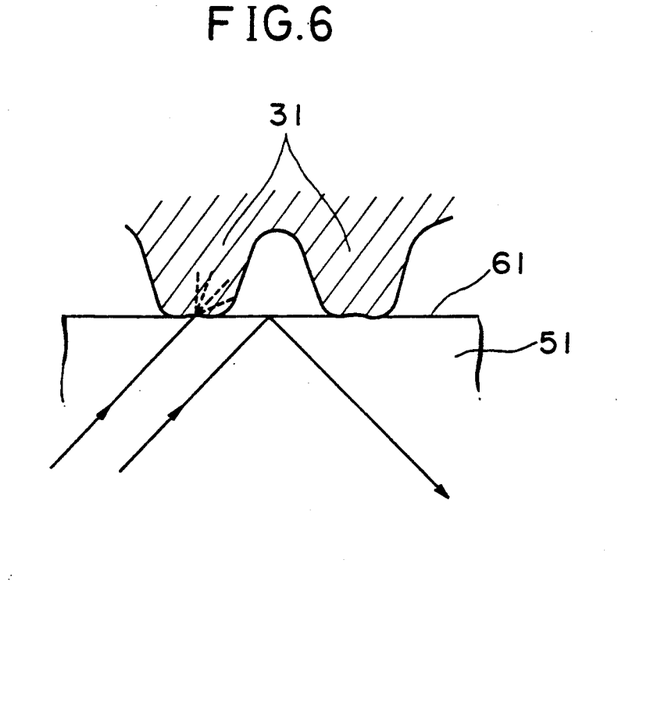
FIG. 6 is a diagram showing light rays scattered or reflected at a boundary on which a finger to be imaged is placed.

The first embodiment will be discussed in more detail with reference to FIG. 6. The rays incident on boundary portions onto which a finger ridge 31 is pressed, are absorbed or scattered by a finger, while the incident rays directed to boundary portions on which a finger ridge are not placed, are totally internally reflected. Since the light detector is arranged to receive mainly the totally internally reflected light, the resulting fingerprint image wherein the ridges are dark and the background bright, is obtained.

A second embodiment will be described with reference to FIGS. 7A, 7B, 8 and 9.

Figure 7A:
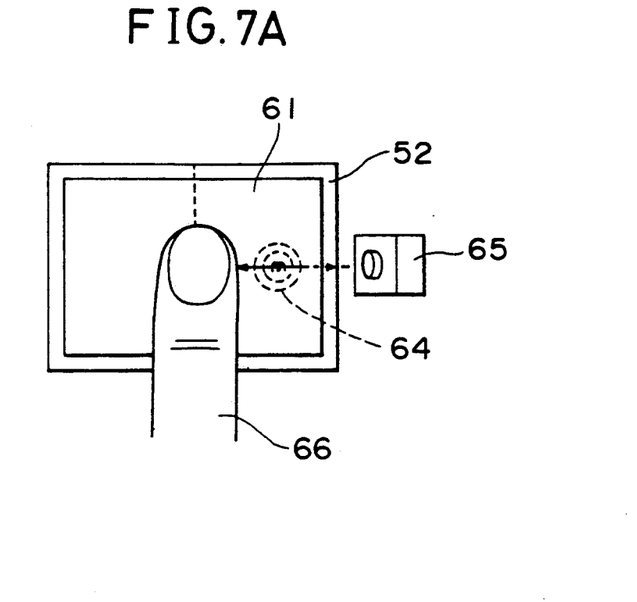
FIG. 7A is a plan view of an fingerprint imaging apparatus according to the second embodiment of this invention.
Figure 7B:
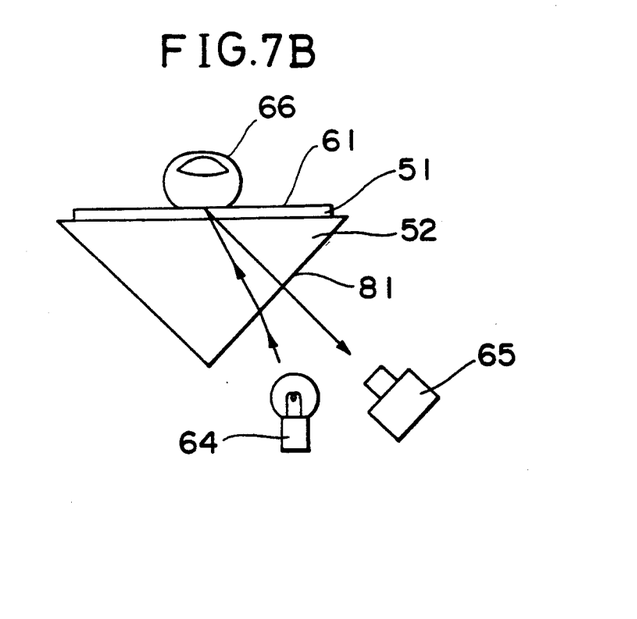
FIG. 7B is an elevation view of the apparatus shown in FIG. 7B.

The second embodiment is of the scattering type and equal to the first embodiment except that the light detector 65 of the second embodiment is positioned to receive the light rays which are scattered at the finger ridge contact portions of the surface 61. FIGS. 7A and 7B respectively correspond to FIGS. 4A and 4B, so that further description thereof will be omitted for clarity.

Figure 8:
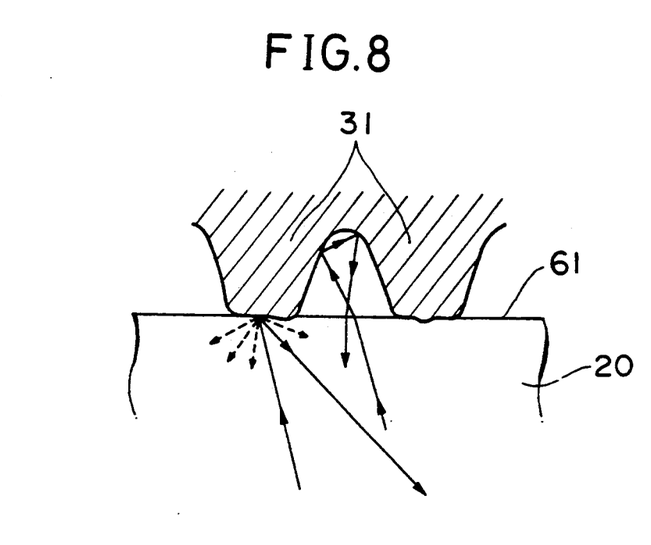
FIGS. 8 and 9 are illustrations for explaining the second embodiment.
Figure 9:
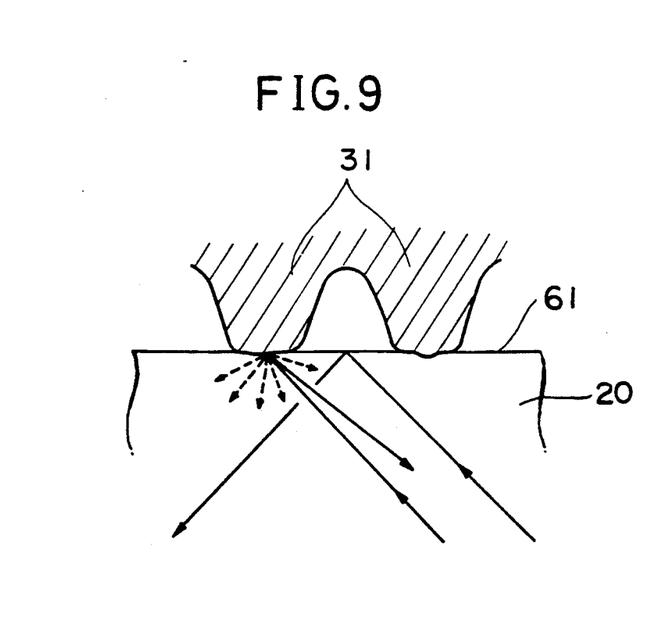

FIG. 8 is an illustration showing light rays scattered and refracted at the surface 61. In this case, the light rays incident on the window portions open to air is refracted. The light detector 65 (not shown in FIG. 8) is arranged to receive the light rays scattered at the window portions against which finger ridges are impressed. On the other hand, FIG. 9 illustrates light rays scattered and totally internally reflected at the surface 61. In this case, the incident light rays are arranged to be totally internally reflected at the surface 61. In the second embodiment, since the light detector is arranged to receive mainly the scattered light emitted from finger ridges, the resulting fingerprint image are such that the ridge portions are bright on a dark background.

Figure 10A:
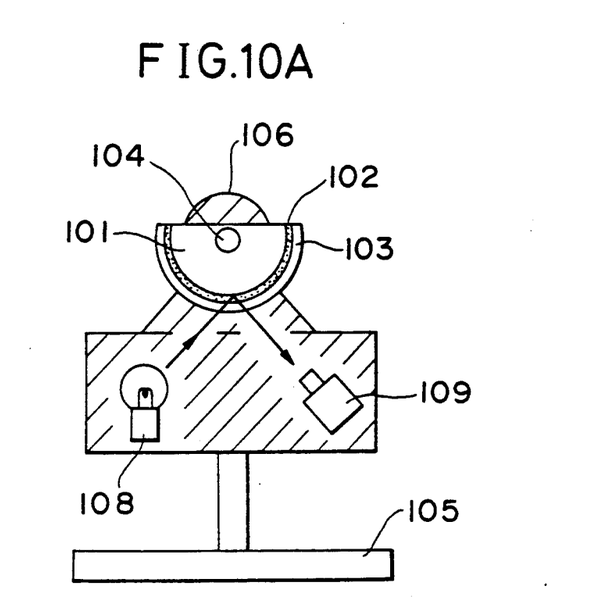
FIG. 10A is an elevation view of the third embodiment of this invention.
Figure 10B:
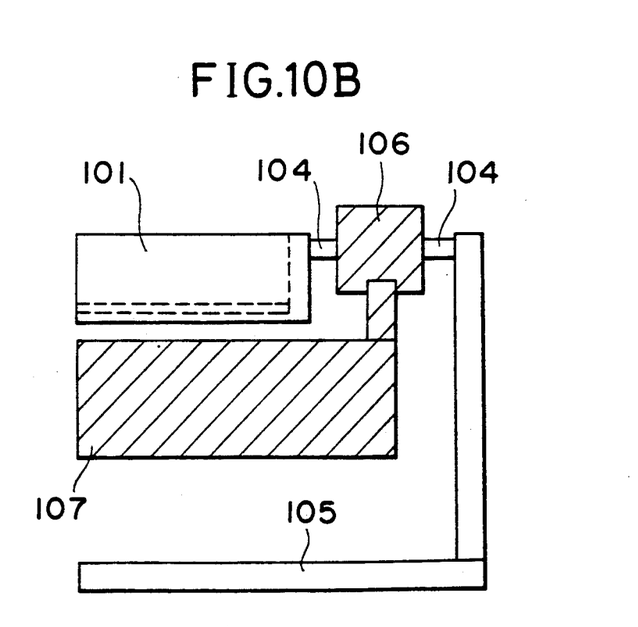
FIG. 10B is a side view of the third embodiment shown in FIG. 10A.

A third embodiment of this invention will be described with reference to FIGS. 10A and 10B. The third embodiment is similar to the first embodiment in that a light detector 109 is positioned to receive total internal light which is reflected from a layer 102. This layer 102 corresponds to the layer 51 in the first embodiment but has a partial cylindrical cross-section for forming an arcuate recess for receiving a finger to be imaged. As a consequence, the layer 102 features a given amount of elasticity and/or viscosity. The third embodiment is provided with an optical assembly 101 which comprises a transparent optical element 103 carrying thereon the above-mentioned layer 102. The optical assembly 101 is secured to an axis 104 around which a driver 106 is rotatably provided. The driver 106 rotates an assembly 107 which includes a light source 108 and the aforesaid light detector 109. The above mentioned assemblies are supported by a supporter 105. A finger placed on the surface of the layer 102 within the recess is optically scanned as the assembly 107 rotates. Such apparatus as the layer 102 is applied as shown in the third embodiment, is disclosed in U.S. Pat. No. 4,537,484 (for example). Therefore, further description of FIGS. 10A and 10B will be omitted for clarity.

Figure 11A:
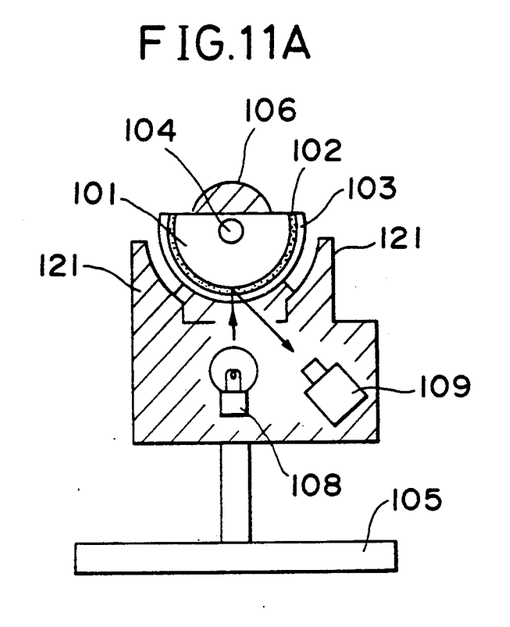
FIG. 11A is an elevation view of the fourth embodiment of this invention.
Figure 11B:
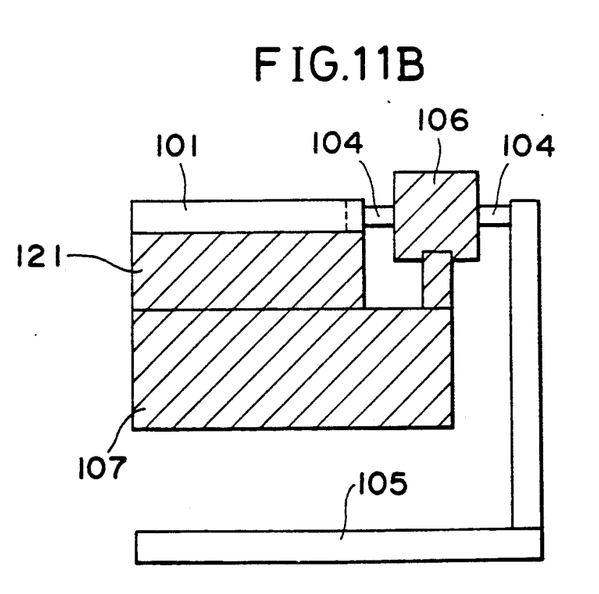
FIG. 11B is a side view of the fourth embodiment shown in FIG. 11A.

A fourth embodiment of this invention will be described with reference to FIGS. 11A and 11B. The fourth embodiment is equal to the third embodiment except that the light detector 109 of the fourth embodiment is positioned to receive light which is scattered at the layer 102. Therefore, the arrangement of the light source 108 and the light detector 109 of the fourth embodiment differs from that of the third embodiment. Another difference between the third and fourth embodiments is that the latter is provided with a light shield 121. This is because the light rays entering the light detector 109 is susceptible to external light.

In the above-mentioned four embodiments, the layer of an elastic and/or viscous material (51 or 102) is placed on the transparent optical element (52 or 103). However, each of the optical elements 52 and 103 itself can be made of such a pliant material.

The foregoing description shows only preferred embodiments of the present invention. The various modifications possible without departing from the scope of the present invention which is only limited by the appended claims will be apparent to those skilled in the art.

What is claimed is:

1. Apparatus for optically imaging a fingerprint, comprising:
    a transparent optical means;
    an elastic layer being provided on a surface of said transparent optical means, said elastic layer being of sufficient elasticity to substantially eliminate any hollow between a finger ridge and a surface of said elastic layer on which the finger is pressed;
    a light source which directs light towards said elastic layer through said transparent optical means, said light source being arranged such that light emitted therefrom is totally internally reflected at said surface of said elastic layer which are not in contact with the finger ridges; and
    a light detector which receives light rays totally internally reflected from the said surface of said elastic layer.

2. Apparatus for optically imaging fingerprint as claimed in claim 1, wherein said transparent optical means has a partial cylindrical cross-section.

3. Apparatus for optically imaging a fingerprint, comprising:
    a transparent optical means;
    an elastic layer being provided on a surface of said transparent optical means, said elastic layer being of sufficient elasticity to substantially eliminate any hollow between a finger ridge and a surface of said elastic layer on which the finger is pressed;
    a light source which directs light towards said elastic layer through said transparent optical means, said light source being arranged such that light emitted therefrom is totally internally reflected at said surface of said elastic layer which are not in contact with the finger ridges; and
    a light detector which receives light scattered at the finger ridges.

4. Apparatus for optically imaging fingerprint as claimed in claim 3, wherein said transparent optical means has a partial cylindrical cross-section.

* * * * *